United States Patent [19]

Møller et al.

[11] Patent Number: 5,772,864
[45] Date of Patent: Jun. 30, 1998

[54] METHOD FOR MANUFACTURING IMPLANTABLE MEDICAL DEVICES

[75] Inventors: Per Møller, Lynge; Jørgen Kamstrup-Larsen, Allerød, both of Denmark

[73] Assignee: Meadox Medicals, Inc., Oakland, N.J.

[21] Appl. No.: 606,086

[22] Filed: Feb. 23, 1996

[51] Int. Cl.⁶ ............................... C25D 1/02; C25D 1/08
[52] U.S. Cl. .................................. 205/73; 205/75; 623/1
[58] Field of Search ................................ 205/67, 73, 75; 427/2.24, 2.25

[56] References Cited

U.S. PATENT DOCUMENTS

| | | | |
|---|---|---|---|
| 1,694,962 | 12/1928 | Berry | 205/73 |
| 2,287,122 | 6/1942 | Norris | 205/73 |
| 2,529,086 | 11/1950 | Law | 205/75 |
| 2,685,507 | 8/1954 | Blood | 419/47 |
| 3,247,579 | 4/1966 | Cattermole et al. | 445/49 |
| 3,457,147 | 7/1969 | Mattia | 205/286 |
| 3,560,350 | 2/1971 | Mattia | 205/73 |
| 3,586,609 | 6/1971 | Jansen | 205/73 |
| 3,939,046 | 2/1976 | Conn et al. | 204/4 |
| 3,947,348 | 3/1976 | Schanernack et al. | 204/9 |
| 4,383,896 | 5/1983 | Pruyn et al. | 428/596 |
| 4,496,434 | 1/1985 | Morssinkhof | 428/596 |
| 4,574,451 | 3/1986 | Smashey et al. | 29/423 |
| 4,600,546 | 7/1986 | Grundei | 264/610 |
| 4,781,721 | 11/1988 | Grundei | 164/34 |
| 5,030,329 | 7/1991 | Haidle et al. | 205/73 |
| 5,042,560 | 8/1991 | Ahlers | 164/34 |
| 5,167,791 | 12/1992 | Herbert et al. | 205/67 |
| 5,199,487 | 4/1993 | DiFrancesco et al. | 165/168 |
| 5,328,587 | 7/1994 | Fenske | 205/73 |
| 5,352,512 | 10/1994 | Hoffman | 428/311.51 |

FOREIGN PATENT DOCUMENTS 1542939  3/1979  United Kingdom .

OTHER PUBLICATIONS

First Thoraxcenter Course of Coronary Stenting, Produced by Peter Ruygrok and Claudia Sprenger de Rover, Rotterdam, The Netherlands, Dec. 15–17, 1994, pp. 5, 13–29.
Programme for Metal Mcromechanical Parts, Feb. 28, 1995, pp. 1–9.
F. A. Lowenheim, Electroplating, McGraw–Hill Book Co., New York, 1978, pp. 426–441, 160–163.

*Primary Examiner*—Bruce F. Bell
*Assistant Examiner*—William T. Leader
*Attorney, Agent, or Firm*—Hoffmann & Baron, LLP

[57] ABSTRACT

An implantable medical device such as an intraluminal prosthetic device is formed by an improved manufacturing process. A generally cylindrical mandrel is provided. A reverse image of the prosthesis is engraved into a portion of the mandrel. The reverse image of the prosthesis defines voids and raised surface areas in the mandrel portion. A prosthesis-forming metallic medium is electrochemically deposited into the reverse image of the mandrel. The metallic medium may be a metal, metal alloy or a metal compound. The mandrel including the prosthesis-forming medium thereon is further processed to separate the prosthesis formed by the prosthesis-forming medium from the mandrel by dissolving the mandrel. The process provides greater design freedom in the formation of flexible expandable stents.

5 Claims, 5 Drawing Sheets

METHOD FOR MANUFACTURING IMPLANTABLE MEDICAL DEVICES

FIELD OF THE INVENTION

The present invention relates generally to a method of manufacturing expandable implantable medical devices. More particularly, the present invention relates to an improved method for forming an expandable micro-sized medical device such as an intraluminal prosthesis directly over a mandrel.

BACKGROUND OF THE INVENTION

The use of implantable medical devices is well known in the art. One type of such implantable device includes endoprostheses for the treatment of diseases of various body vessels. Intraluminal devices of this type are used to hold open or otherwise support an occluded body vessel and are commonly referred to as stents. Stents are typically intraluminally implanted by use of a catheter into various body passageways in the vascular system, the bile tract and the urogenital tract for the primary purpose of holding an otherwise occluded area open. In some instances they are used in combination with grafts to repair a weakened vessel. Such stents are radially compressible and expandable so that they may be easily inserted through the lumen in a collapsed or unexpanded state. Once properly positioned, the stent may be deployed by allowing it to self-expand to an uncompressed state or by expanding the stent by use of a catheter balloon.

As stents are normally employed to hold open an otherwise blocked, constricted or occluded lumen, the stent must exhibit a high degree of radial or hoop strength in its expanded state. In addition, balloon-expandable stents must have sufficient structural integrity and material density to allow for plastic deformation. Thus, the stent structure must be strong enough to undergo localized stretching and expansion beyond the plastic limit of the material in order for permanent expansion of the stent to occur. Moreover, the density of the material must be balanced with the tensile strength, hoop strength and other mechanical properties that will depend to a certain degree on the lattice or crystalline structure within the material.

Also, the stent is often transported to the desired location in the body through narrow tortuous paths, such as the vessels of the vascular system, and final positioning of the stent may be at a curved location. Thus, the stent must be sufficiently flexible so that it may be easily maneuvered and located without harm to the body. The particular design of the stent geometry, as well as the materials which form the stent, are critical in providing a device which is sufficiently maneuverable in the winding and constrictive passageways of the vascular system, but also must exhibit sufficient strength to enable the stent to function for its intended purpose.

In this regard, numerous materials have been employed in the manufacture of stents. Such materials may include stainless steel and metal alloys which impart sufficient rigidity to the stent. Further, other materials such as nitinol may be employed. The use of nitinol enables the stent to expand or contract upon changes in temperature without deforming the stent in a non-elastic manner.

The prior art formation of stents has been accomplished by one of two basic techniques. The first technique is generally referred to as a wire forming technique. This technique employs single or multiple strands of wire such as stainless steel, which are wound into a shape such as a mesh, coil, helix or the like, about a smooth cylindrical rod-like mandrel. The stent resulting from this manufacturing technique is highly flexible and readily expandable. The spaces formed between the coiled wire permit such flexibility and expansion. Examples of such wire formed stents are shown in U.S. Pat. No. 4,866,062 to Wiktor, U.S. Pat. No. 4,800,882 to Gianturco and U.S. Pat. No. 4,856,516 to Hillstead.

Another technique used to form expandable stents is by the use of solid cylindrical tubes as stent preforms. Such tubes may be formed into a stent by etching or otherwise cutting voids into the tube to form the spaces in the solid material which enable the stent to expand. Examples of this technique for forming stents are shown in U.S. Pat. Nos. 4,733,665, 4,739,762 and 4,776,337 all to Palmaz. Moreover, manipulating a wire preform is difficult when the geometric structure of the stent is complex and/or the size is very small. The efficiency and cost of producing microstents is therefore an issue.

While these forming techniques provide stents which may function as intended, each of these techniques has several limitations. With respect to the wire formed stents, while the stent design provides for increased flexibility and ease of expansion, the stent so formed may lack adequate structural stability. Additionally, to manipulate the preform into a stent requires stressing the material in order to impart the angle or sinusoidal curvature at the points of expansion. With respect to etched tube forming of stents, while the openings between the solid members of the stents are generally smaller than wire formed stents, stents of this type are relatively inflexible. This results in increased difficulty in maneuvering the stent through the body lumen and prevents longer stents from being located in body vessels. Furthermore, machining or etching of a preform is required to form the stent, all of which is time and cost intensive.

Both of the prior art forming techniques are limited by size and shape. This is largely because they are formed from a pre-form which is then either shaped into the stent or material is cut out to form the stent. Micro-sized stents and other medical devices which are designed for very small areas in the body are not easily made using such techniques. For example, a wire-formed stent is made by shaping a wire into a geometric pattern and/or wrapping it around a mandrel. Shaping wires into complex geometric patterns is difficult when the device is intended to be very small and a large number of bends in the wire is necessary to form the geometry. Furthermore, the thickness of the wire is also a consideration, since the wire must be easily shaped yet possess sufficient strength for its intended purpose. Similar considerations with respect to wall thickness and complexity of geometric pattern must also be given to stents formed by etching spaces in preformed hollow tubes.

Thus, an inherent limitation of both known stent manufacturing techniques is that due to the metal shaping techniques employed, there is very little design freedom available in constructing the geometric configuration of the stents. It is difficult to construct such stents in anything but simple basic configurations. Also, the dynamic parameters of the stent, such as flexibility, as well as rate and degree of expansion, are difficult to control with the stents designed by the prior art techniques. The prior art manufacturing techniques further limit the types and varieties of materials which can be used to form stents. The materials employed as well as the techniques for forming the stents have a tendency to result in stents having surface imperfections. These imperfections could compromise the long term patency of the stent.

It is therefore desirable to provide a manufacturing technique which will provide more design freedom, provide better controls of the mechanical properties and dynamic parameters of the stent and which permits the use of various stent materials in the formation of the stent. The present invention also addresses the problems of reproducibility and cost efficiency.

SUMMARY OF THE INVENTION

It is therefore an object of the present invention to provide an improved method for manufacturing an implantable medical device and in particular an expandable intraluminal prosthesis.

It is a further object of the present invention to provide an improved method for forming an expandable intraluminal prosthesis where the configuration of the prosthesis is formed directly on a mandrel without a wire or tubular preform.

It is still a further object of the present invention to provide an improved method for manufacturing intraluminal prosthesis where significant freedom is provided in the geometric configuration of the stent as well as the material used to form the stent.

It is yet a further object of the present invention to provide a method of making highly precise dimensionally stable micro-structures which can be used for expandable medical implants such as stents and which can be particularly adapted to accommodate and support a graft structure.

In the efficient attainment of these and other objects, the present invention provides a method for forming an elongate expandable intraluminal prosthesis. An elongate mandrel is provided having aL reverse image of the prosthesis formed in a surface portion thereof. A prosthesis-forming material is deposited into the reverse image of the mandrel. The mandrel is further processed to separate the prosthesis formed by the prosthesis-forming material from the mandrel, while leaving the prosthesis intact.

As more particularly described by way of the preferred embodiments herein, the mandrel may be formed with a reverse image, such image including a pattern of voids formed in a predetermined geometric pattern. This may be accomplished by a number of methods, including engraving the geometric pattern into the surface portion of the mandrel. Other machining methods may be useful in forming the reverse image pattern on the mandrels, as well as injection molding or cast molding of the mandrel. The voids formed in the mandrel are filled with prosthesisforming materials or medium by various deposition techniques. The prosthesis-forming material includes a fluid metal or metal alloy. The metal is deposited into the voided geometric pattern of the material and solidifies to form the prosthesis. At this point the mandrel and the prosthesis are integrated. Thereafter, the thus formed prosthesis is removed from the mandrel, preferably by dissolving the mandrel and leaving intact the formed prosthesis. Further, in depositing of the prosthesis-forming material, in addition to filling the voided geometric pattern, the entire surface portion of the mandrel may also be initially covered with the fluid metal. In such a case, the mandrel may be further processed to remove the metal from those surface portions at all areas except the voids. Subsequent removal of the mandrel results in the formed prosthesis.

The techniques disclosed for depositing the fluid metal onto the conductive mandrel include electrochemical plating from solution. Such solutions are preferably aqueous but may also in some cases be organic.

DETAILED DESCRIPTION OF THE PREFERRED EMBODIMENTS

The present invention provides a manufacturing technique for producing improved high quality implantable medical prosthetic devices and in particular micro-sized endovascular prosthesis such as stents for use in a variety of medical applications. The process of the present invention allows for virtually unrestricted freedom in designing the geometry of the device, because the mandrel upon which the device is formed is first provided with the reverse image of the device. The reverse image comprises a geometric pattern of virtually any size, shape and configuration. This geometric pattern is formed into the mandrel to create voids or grooves into which is deposited the prosthesis-forming material or medium, thereby forming the prosthesis. The geometric pattern and its physical measurements are chosen based on the type of device and its intended use. This inventive process is especially designed to produce high quality micro-devices without subjecting the preform material to the mechanical forces required to bend, shape or cut-away the preform and form the final device. One required aspect of the mandrel used is that it must be of a conductive material which is sufficiently strong enough to keep the electroplated stent intact during subsequent machining steps. The mandrel must also be made of a solid, non-flowable material such that it will hold the micro-sized reverse image which is machined, e.g. engraved into the surface. At least one prior art method disclosed in British patent 1,542,939 uses wax as a mandrel for making a metal bellow. The wax mandrel is filled with electrically conductive particles. Electro-depositing of metal is performed on the molded wax pattern and the wax is then melted or dissolved away. This reference discloses that solid walled hollow bellows can be made from this technique. In the present invention, however, such soft mandrels do not give the sharpness of the geometry and configuration required for "open-celled" micro-structures such as stents. Thus, solid conductive mandrels, such as metallic mandrels on which can be micro-engraved a reverse image of the stent, are used.

This method is contrary to prior art practices where preforms, either in the form of a thin metallic wire or a thin-walled tube, must be subsequently modified to form a particular stent construction. The advantages of the present invention allow the stent to be designed to specific parameters such as degree of flexibility, rate of expansion and the like for various particular applications. Further, the inventive techniques used to form the stent provide for improved surface finish without imperfections which normally result from formation using prior art methods. The resulting stent has improved properties and improved long term patency.

Figure 1:
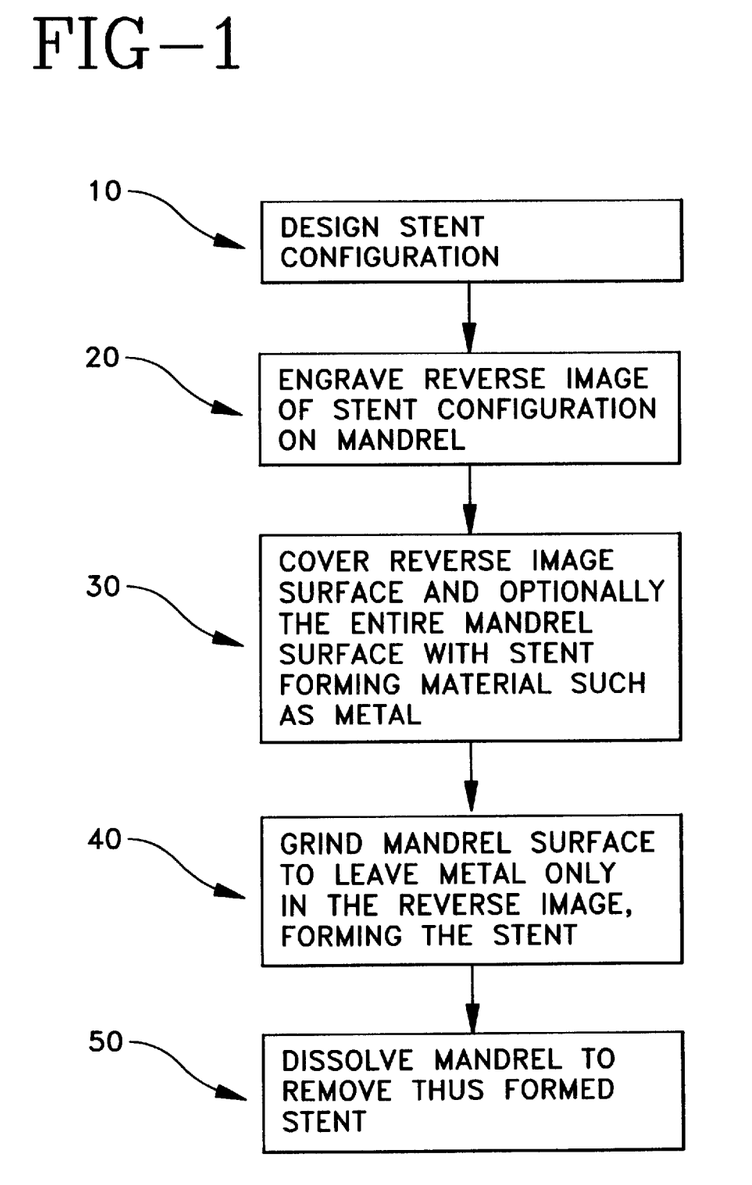
FIG. 1 is a flow chart showing steps employed in the manufacturing process of the present invention.

Referring to FIG. 1, the first step 10 employed in the process of the present invention is to design a particular stent configuration. After the particular configuration is designed, the second step 20 includes forming, e.g. by engraving the reverse image of the stent configuration designed in first step 10 on a forming mandrel. The third step 30 includes covering the reverse image portion with a stent-forming material. Although the reverse image portion may be selectively covered with the stent-forming material without depositing any material on the other portion of the mandrel, it is optional to do so and if the entire mandrel is covered with the stent-forming material then the forth step 40 includes grinding the mandrel surface to leave stent-forming material only in the reverse image of the stent. The final step 50 is to dissolve the mandrel to leave the resulting stent.

Design of Stent Configuration 10

The present invention contemplates increased freedom in design in that the stent can be designed to have a geometry which exhibits various desired characteristics. Such characteristics may include enhanced flexibility, predetermined radial expansion, as well as sufficient stent density to provide adequate structural stability for vessel support. Since the stent to be formed is formed directly on the mandrel itself without need for further processing of the work piece, near total design freedom is provided by the method of the present invention.

It is contemplated that techniques of computer aided design (CAD) may be employed to design the specific geometry of the stent configuration. Parameters such as desired rates of expansion, size of the stent and particular materials employed can be used in combination with computer aided design to define a particular optimum stent geometry.

Formation of Mandrel 21

Figure 2:
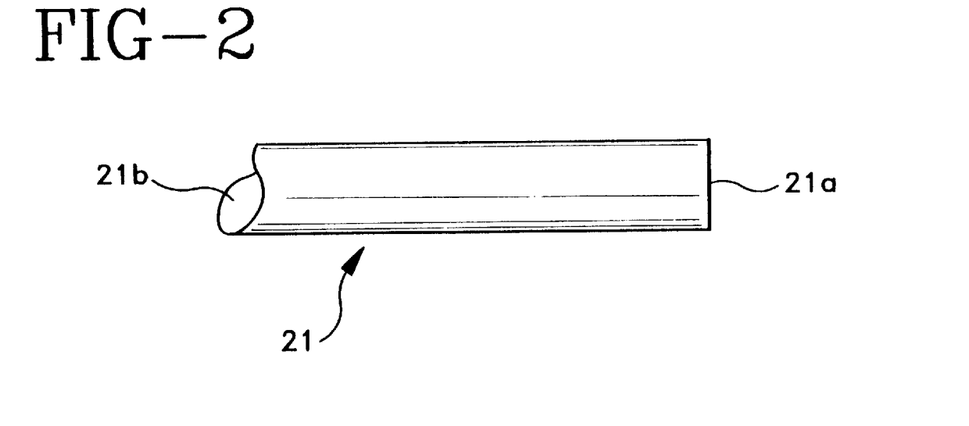
FIGS. 2–7 show individually the successive steps employed in the manufacturing process of the present invention.

Once the particular stent geometry is selected, a cylindrical forming mandrel 21 shown in FIG. 2 may be employed. Mandrel 22 is an elongate rod-like cylindrical member having opposed ends 21a and 21b. Mandrel 21 may be formed of various materials. While a metallic mandrel is preferred, it is also contemplated that the mandrel may be formed of sufficiently dense and hard polymeric material coated with a metallic coating. In the present illustrative embodiment brass is selected as the preferred material because it is a material which is conductive, may be easily engraved and easily dissolved. As previously mentioned, one requirement of the mandrel is that it be sufficiently strong to allow an engraved pattern to be formed on its surface. Since the stent pattern is generally an open-celled configuration, designed to allow for plastic deformation when expanded, it is important that the mandrel be made from a material which is sufficiently hard to hold the sharpness of the complex micro-sized patterns required for stents. As previously mentioned, soft materials such as wax are not capable of holding such a sharp pattern due to their flowability and low melting point. Thus, for purposes of this invention, a metallic or metallic-coated mandrel is generally required, since it has the requisite solid density necessary to serve as the reverse image substrate for a subsequently formed electroplated stent. Although brass is the preferred material, since it can be easily dissolved in solution when separating the stent from the mandrel, other metals and/or alloys may be used. The choice of the material for the mandrel will depend on whether its surface is sufficiently hard and dense to have an accurate and potentially complex reverse image pattern engraved thereon, as well as its ability to be dissolved in solution. Thus, the dissolving solution and the electrically conductive mandrel must be chosen such that the stent can be formed and separated from the underlying mandrel without destroying or causing defects in the surface of the micro-sized stent device. Thus, when choosing the mandrel material, close attention must be paid to these consideration.

Machinery for producing the reverse image on the surface of the mandrel may vary depending on the complexity of the geometric pattern, type of material used for the mandrel as well as other consideration. Fine cutting heads or tools may be used to machine the micro pattern, or etching or molding may be possible in some instances. Micro-machining of the mandrel to form the reverse image for the prosthetic device can be accomplished by a number of fabrication techniques. For example, wet etching can be used to create microstructures that are well defined. Such etching can be isotropic, i.e. the same etching rate in all directions, or anisotropic, where certain directions in the crystal are etched much faster than others. Isotropic etching of Al, Zn and stainless steel is widely used. Silicone substrates are also used with an aqueous solution of potassium hydroxide.

Electrochemical machining can also be used, whereby passive or hard materials such as steel, brass or titanium can be machined applying high potential, i.e. 100 volts or more. The electrolyte used is salt water or diluted acid. The electrolyte is pumped at high pressure into the area being dissolved, thereby cooling the surface and removing dissolved metal hydroxides.

Electro-discharge machining is used to create silicon or metal microstructures. This process is slower than the other techniques and is generally employed when the mandrel is to be reused, as in the present invention. For example, this technique can be used using brass or copper.

Other types of micro-machining, such as by using lasers can be used on most materials.

The reverse image which is formed on the surface of the mandrel must be free from micropores or defects, since the quality of the subsequently formed electroplated stent will depend on the surface quality of the engraving. Thus, subsequent to mechanical formation of the reverse image, chemical etching or other polishing techniques may be required to remove surface imperfections and burrs, thereby enhancing the surface finish. Generally, engraving or machining of the reverse image is conducted in the presence of a lubricating oil which also must be removed prior to electroplating. One means of accomplishing this is to place the mandrel in an electrolytic cleaning solution, which removes any oils, oxides and other particles which would potentially interfere with the adherence of the electroplated stent material to the mandrel. Brass mandrels contain a large amount of copper, which is known to be easily oxidized. A current density of between 5–10 amps/dm$^2$ is generally used. For instance, in the case of a brass mandrel, the mandrel is connected to a cathode in a cyanide solution. Cyanide has excellent complexing properties with certain oxides, such as copper oxide and the release of hydrogen from the solution serves to bubble away grease and oil which remains on the mandrel surface as a result of the engraving process. Other electro-cleaning compositions include sodium hydroxide, sodium cyanide and sodium carbonate. In the case of sodium hydroxide, this solution serves to hydrolyze the oils and form a sodium salt of the oil. Sodium carbonate provides excellent wetting of the surface, similar to a surfactant.

Once the mandrel has been electro-cleaned, it is generally rinsed with deionized water to prevent contamination of the next pretreatment solution, which is usually a chemical polishing solution designed to remove surface defects. In particular, raised portions of the surface, such as burrs, are generally polished using peroxide/sulfuric acid systems to round out the corners and remove the sharp edges. Uniformity and smoothness of the surface is particularly important when electroplating of the stent is to be performed. Such activation solutions are chosen based on the type of mandrel metal used, since various salt films form depending on the mandrel material. Furthermore, organic films should be removed as well, and dipping in acidic solutions such as hydrochloric acid or nitric acid remove such films, as well as certain deposits of lead. Even if polishing of the surface is not required, activation of the surface by removal of oxides and other salt films is important for proper deposition of the electroplated stent. organic films are often times a result of the polishing step. In instances where lead is abundant on the surface, citric acid can be used to remove such deposits. Activation is generally performed by quickly dipping or otherwise applying the activation solution to the mandrel surface for about 30 seconds to one minute.

Figure 3:
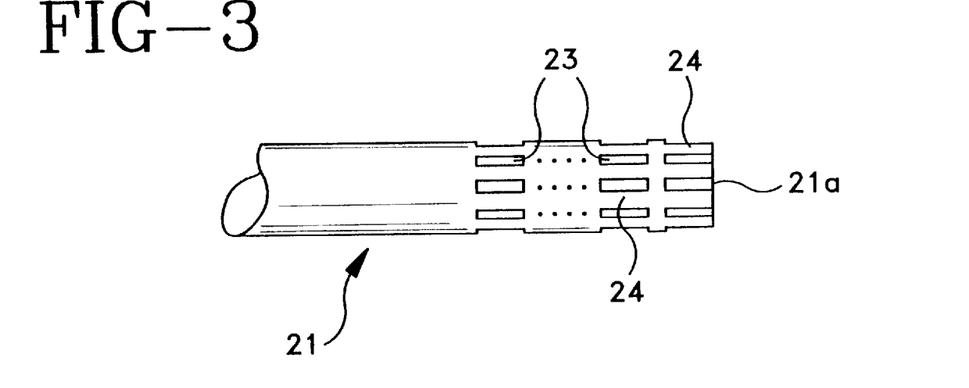

With respect to FIG. 3, brass mandrel 21 may be further processed to include adjacent end 21a thereof a reverse image 22 of the desired stent configuration. Reverse image 22 includes a series of voids 23 and spaced apart raised sections 24 defining the reverse image. The engraving technique which places the reverse image 22 into the end 21a of stent 21 may be a conventional engraving machine (not shown) which may be computer controlled in combination with the CAD designed geometric configuration to provide the precise reverse image pattern on mandrel 21. Further techniques such as spark erosion may also be employed.

Covering of Mandrel With Metal 30

Once the reverse image 22 is formed in the end 21a of mandrel 21 and the above-mentioned surface treatments have been accomplished, the end 21a may be covered with a stent forming material 31. The stent forming material 31 is deposited or placed in the reverse image 22 formed in the mandrel 21. The material may also cover the end 21a of mandrel 21 and would be subject to further processing as described hereinbelow.

The stent forming material 31 is deposited in the reverse image 22 of mandrel 21 by electro-chemical deposition.

Electrochemical Deposition (ECD) is here defined as a process for deposition of metal/metal alloys or metal compounds on a base material (mandrel) by electrolysis from aqueous solution, organic solution or salt melts. Electrochemical deposition is employed in the present invention because it yields a density in the electroplated stent which is nearly identical to the density of the metal itself as defined in the periodic table. As previously mentioned, proper density of the solid micro-sized stent device is important to the structural and mechanical end properties of the resultant device. In addition to density, the thickness of the stent, as well as the crystalline arrangement of the metal atoms must be sufficient to allow elongation and expansion of the material without compromising the structural integrity when the stent undergoes balloon expansion. Electrochemical plating from solution provides proper density, thickness and crystalline lattice structure such that the required end properties can be controlled. On the other hand, vapor deposition techniques, whereby coatings are formed by deposition of atoms or groups of atoms from the gaseous phase, provide coatings which are normally extremely small and would not be sufficiently useful to produce open-celled, micro-sized structures which would have the mechanical properties to produce a stent. For example, vapor deposition produces densities which are less than 100% of the metal as it occurs in nature. The coatings or layers which are formed using vapor deposition are usually on the order of nanometers or angstroms. Thus, prior to the present invention, processes such as vapor deposition would not be expected to produce stents which would be commercially viable.

Electrochemical deposition of metals generally employs electrolytes at temperatures from about 25° C. to about 70° C. The electrolyte can be an aqueous or organic solution containing a suitable salt of the metal or organometallic compound dissolved in the electrolyte. The electrolyte must be a relatively good electrical conductor in order to get good distribution of the material. Complexing agents and pH values must be within certain ranges such that the reduction of metal occurs before the reduction of hydrogen. Electrodeposition of the metal is also possible from a saltmelt. Particularly, Nb Ta and Pt may be plated from saltmelts.

Metals that are plated from aqueous solutions can be divided into two groups. The first group is electroplatable elements and the second group is elements that can be reduced chemically, i.e. eletroless plating. For example, electroless plating is possible with elements such as Co, Ni, Cu, Pd, Ag, Au, and Sn. The driving force in chemical plating is the reducing agent. When the metal is reduced, the reducing agent is oxidized and must be replinished together with the metal used. As a result, oxidized reducing agents can build up, as well as other ions which may be present if metal salts are used. As a result, electroless plating baths are not as stable and have a limited lifetime. However, electroless plating is useful when attempting to create metal coatings on non-conducting materials such as polymers, ceramics and glass. Thus, in the present invention, it is anticipated that electroless plating is not a preferred embodiment. Chemical additives may be employed along with the electrolyte in order to change the properties of the deposition of metal. Typical properties that can be altered through the use of additives include hardness, internal stress, smoothness and structure, i.e., laminar growth versus column growth. The addition of such additives can have a levelling effect to the surface, thereby improving smoothness of the surface.

Pulse plating, which uses pulsating current to electrochemically deposit the metal, can also be used to change the properties of the resultant deposit.

The use of multi-layered deposits whereby different metals or alloy compositons are combined in layers on the mandrel, may also be employed. The properties of such multi-layered deposits in many cases exceed the properties of the individual metals themselves. In particular, tensile strength and magnetic properties have been known to be greatly enhanced. Such multi-layered deposits can be produced by dual bath processes or by a single bath process. The dual bath process involves the use of two separate electrolytes, whereby the substrate is moved from one bath to the other. In the single bath system, layers are applied in succession by alternating or pulsing the current.

During deposition of the stent forming material, one main objective is to provide good adhesion between the metal and the mandrel, while allowing for easy dissolution of the mandrel once the stent is formed. Several coatings of metal can be used, one over the other, the first coating being chosen to prevent build-up of unwanted surface residues prior to deposition of the final stent forming material. This first layer is intended to be dissolved away with the mandrel substrate. For example, in one alternative embodiment, rather than directly deposit the stent forming material on the surface of the mandrel, a first metal can be deposited on the mandrel, for example, nickel, which can prevent the formation of dendritic build-up of metals which may form when the mandrel is dipped into the electroplating bath, but prior to application of the electric current. These dendritic surface structures would prevent good adherence of the stent forming material due to their sharp corners. Thus, a variety of different layers of electrochemically deposited metals may be employed for specific purposes.

A number of different materials can be used as the stent forming material. In particular, the choice of material will depend to a large degree on its ability to be used as a safe and efficacious implant material. Among the mechanical properties which the metal should possess include the ability to be formed into a stent which has good elongation, tensile strength and elasticity and ductility properties. It must be fatigue resistant so that it can bend numerous times in the same area without breaking. It must be capable of being deformed beyond its elastic limit via balloon catheter while maintaining its structural integrity for use as a prosthetic device. In some instances, radio passivity is also important. Metals which can be plated from an aqueous solution include Cr, Mn, Fe, Zn, As, Se, Tc, Ru, Rh, Cd, In, Sb, Te, Re, Os, Ir, Pt, Hg, Ti, Pb, Bi. Those metals which can be plated from organic based electrolytic solutions include Ti and Al, as well as others. Additionally, numerous metals can be plated as an alloy of the foregoing water based electroplated metals. For example, B, Ga, Ge, P, S, V, Nb, Mo, and W can be plated as an alloy of the previously mentioned metals which are plated from an aqueous solution. Finally, metals such as Co, Ni, Cu, Pd, Ag, Au, and Sn, can be plated without an electric current, i.e. electroless plating.

The liquid electrochemical bath can therefore be an aqueous solution, a melt of a salt, e.g. a fluoride based melt, or a metal/organic solution.

Among the various materials used, gold has been found to be extremely useful because of its inertness to the body, and because it possesses many of the mechanical characteristics necessary for a commercial stent. Alloys of gold and alloys of wolfam (W) are also useful. Gold/ silver solutions can also be used. The plating of a sandwich structure containing two or more layers can be done by layering, i.e. using different bath solutions in succession. Additionally, a composite bath can be used and the deposition potential varied to plate the different metals successively.

The amount of metal required in the electrochemical solution is dependent upon the mechanical properties desired. For example, if a gold/sulfite bath is formed, about 9–10 grams per liter of gold is used in an aqueous sulfite solution. The amount of gold is maintained relatively constant in the bath as the electroplating process removes gold for deposition on the substrate. As previously mentioned, the temperature of the plating bath will vary from room temperature to about 70° C. and more typically about 40° C. The current density used in applying the solution will also affect the mechanical properties. Additionally, plating time depends upon the current density and the latter can be selected based on a number of factors. Such factors include temperature, bath composition, thickness desired, and pH. For example, the pH of a gold/sulfite bath is typically about 6.5, but pH values may also vary between 3–4. Plating can take from about 2–12 hours based on the type of material and the above-mentioned factors. Additives can be added to the baths for their intended function. In acid/gold baths, sometimes small amounts of nickel and cobalt are added.

Subsequent to electrochemical deposition plating, a rinsing step is preferably performed and any excess deposited metal, i.e., gold is machined away. The stent is thus formed. In the instance where deposition of the stent forming material has coated the entire mandrel, grinding can be performed to leave the metal only in the engraved portion. Additionally, grinding can be performed on the stent per se to remove imperfections or polish the surface. Such grinding can be done a number of ways, including centerless grinding. The outer diameter of the finished stent is thus easily controllable.

In preferred embodiment of the present invention, various bath formulations may be employed to plate or coat the end 21a of mandrel 21. Examples of such preferred embodiments which use ECD include the following:

Formulation for Copper-bath used for deposition on the mandrel to produce implantable prosthesis:

| | |
|---|---|
| Copper sulfate ($CuSO_4$, $5H_2O$) | 60–90 g/l |
| Sulfuric acid ($H_2SO_4$) | 150–225 g/l |
| Chloride (Cl) | 30–80 mg/l |
| Temperature | 20–35° C. |
| Cathode current density | 0.5–5 Amp/$dm^2$ |
| Plating speed by 3 Amp/$dm^2$ 0.66 microns/min | |

Formulation for Silver-bath used for deposition on the mandrel to produce implantable prosthesis:

| | |
|---|---|
| Silver cyanide (AgCN) | 31–56 g/l |
| Potassium cyanide (KCN) | 50–78 g/l |
| Potassium carbonate ($K_2CO_3$) | 15–90 g/l |
| Temperature | 20–38° C. |
| Cathode current density | 0.5–1.5 Amp/$dm^2$ |
| Plating speed by 1 Amp/$dm^2$ 0.64 microns/min | |

Formulation of Nickel-bath used for deposition on the mandrel to produce implantable prosthesis:

| | |
|---|---|
| Nickel sulphamate ($Ni(SO_3NH_2)$ $4H_2O$) | 340–360 g/l |
| Nickel chloride ($NiCl_2$, $6H_2O$) | 6–7 g/l |
| Boric Acid ($H_3BO_3$) | 30–40 g/l |
| pH 4–4.5 | |
| Temperature | 45–60° C. |
| Cathode current density | 0.5–5.5 Amp/$dm^2$ |
| Plating speed by 4 Amp/$dm^2$ 0.8 microns/min | |

Formulation of Gold/Silver-bath used for deposition on the mandrel to produce implantable prosthesis (12 carats gold):

| | |
|---|---|
| Potassium gold cyanide ($KAu(CN)_2$) | 8–9 g/l |
| Silver cyanide (AgCN) | 3.6–3.8 g/l |
| Potassium cyanide (KCN) | 75–85 g/l |
| pH 11.5 | |
| Temperature | 42–47° C. |
| Cathode current density | 0.8–1.2 Amp/$dm^2$ |
| Plating speed by 0.9 Amp/$dm^2$ 0.5 microns/min | |

Formulation of Gold-bath used to for deposition on the mandrel to produce implantable prosthesis (24 carats gold):

| | |
|---|---|
| Potassium goldsulfite ($K_3Au(SO_3)_2$) | 19–21 g/l |
| NaEDTA | 29–31 g/l |
| Sodium Sulfite $Na_2SO_3$ | 85–95 g/l |
| pH 10 | |
| Temperature | 40–60° C. |
| Cathode current density | 0.1–0.5 Amp/$dm^2$ |
| Plating speed by 0.3 Amp/$dm^2$ 0.2 microns/min | |

In each instance some form and duration of agitation of the bath may be necessary. Such agitation may include mechanical or air agitation or a combination thereof.

Figure 4:
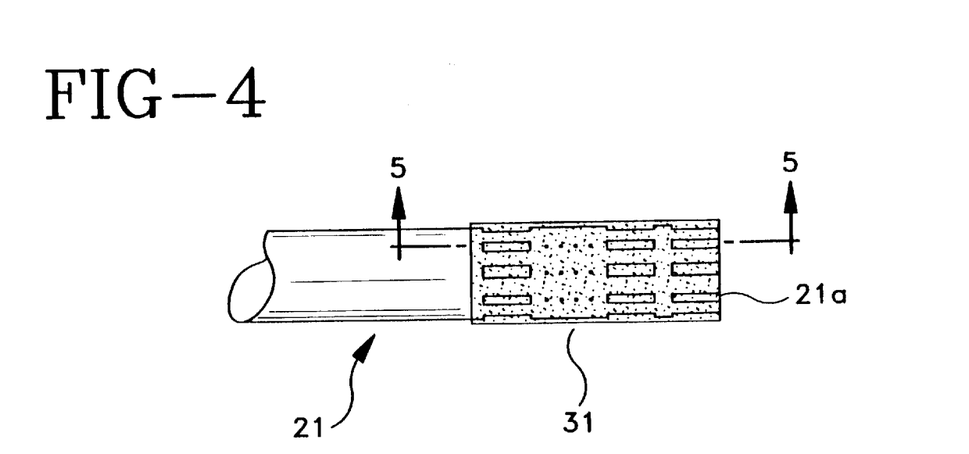
Figure 5:
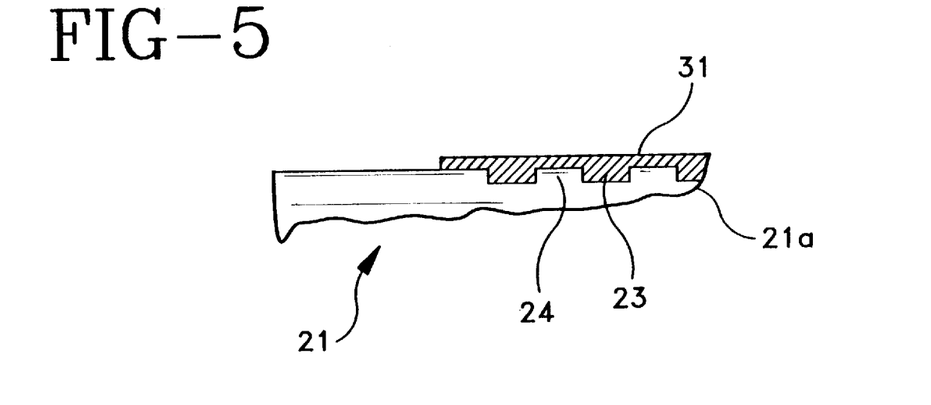

As is shown in FIGS. 4 and 5, the stent forming material 31 covers the entire end portion 21a of mandrel 21 including filling the voids 23 as well as covering the raised surfaces 24 of reverse image 22.

Grind Nandrel Surface 40

Figure 6:
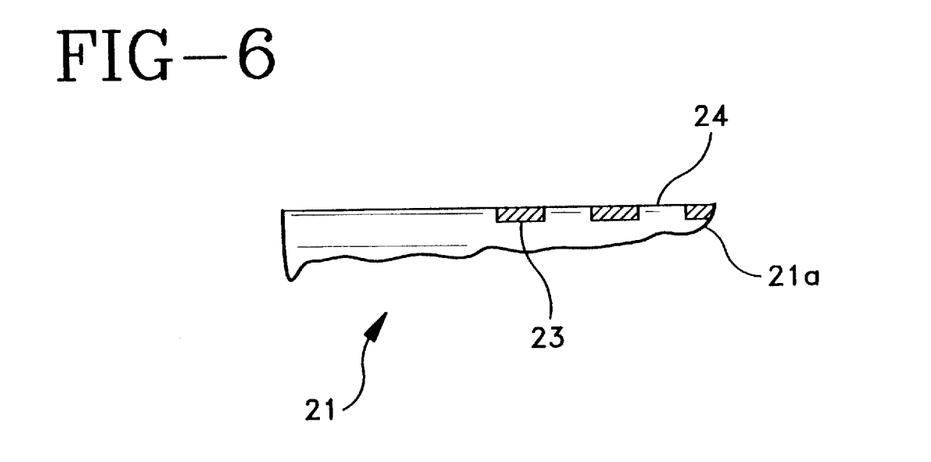

As shown in FIG. 6 in accordance with the present invention, the mandrel 21 is further processed so as to grind the stent forming material 31 from the raised surfaces 24 of reverse image 22 so that stent forming material 31 exists only within the voids 23 of the reverse image 22.

Dissolving Mandrel 50

Figure 7:
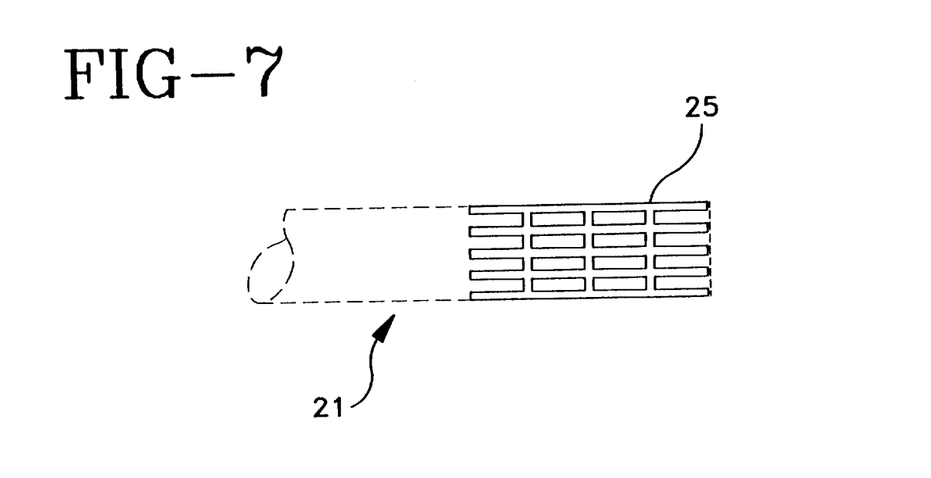

Thereafter, as shown in FIG. 7, mandrel 21 may be dissolved so as to leave remaining only the resulting stent 25. As previously mentioned, the solution used to dissolve away the mandrel is to be selected based on the choice of mandrel material, as well as the choice of stent forming material. One preferred embodiment of the stent involves using a brass mandrel, a gold or gold alloy stent forming material and nitric acid as the dissolving bath.

Figure 8:
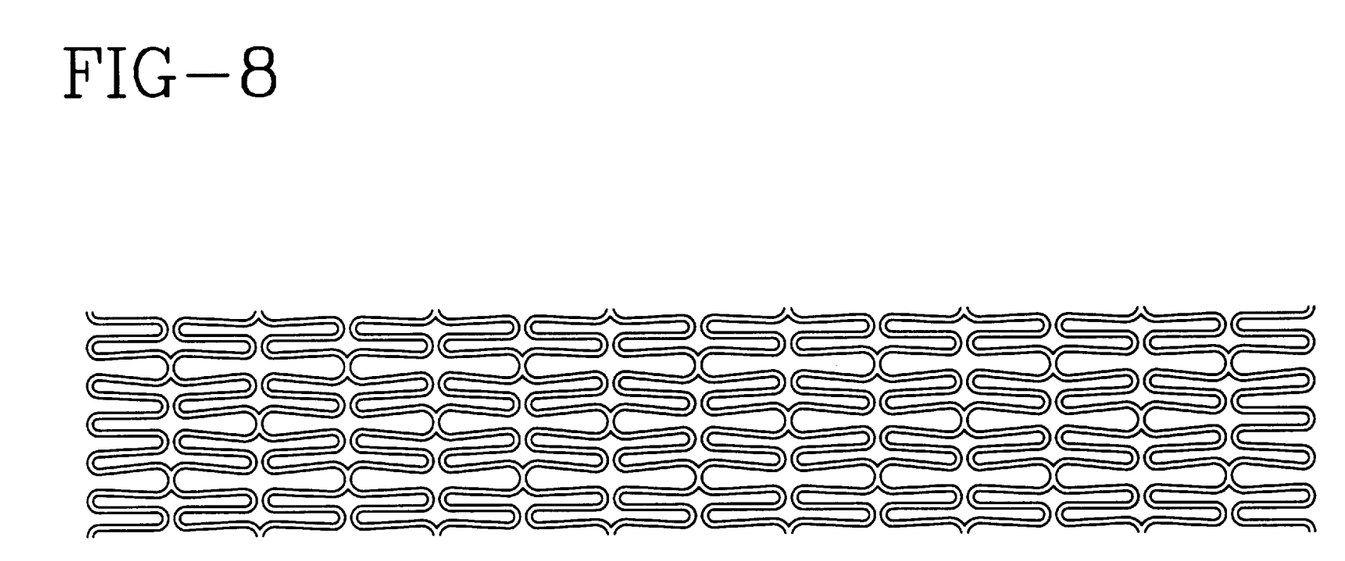
FIGS. 8 and 9 show specific embodiments of stents formed by the process of the present invention.
Figure 9:
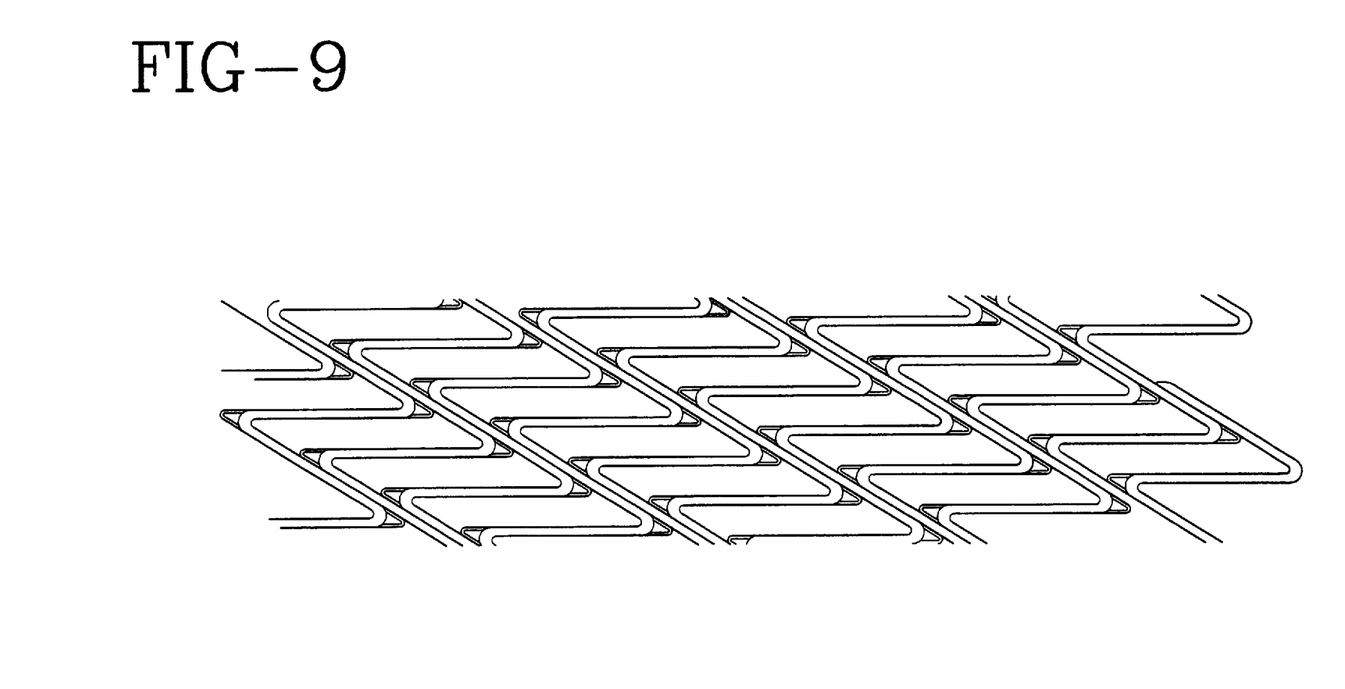

FIGS. 8 and 9 show typically examples of stents 25 which may be formed from the process of the present invention. The present invention allows for complex or intricate stent geometry to be formed in accordance with the above-described process. These various stent geometries, examples of which are shown in FIGS. 8 and 9, may be of the type which are computer-generated based on various factors, such as rate of stent expansion, radial or hoop strength desired, and amount of wire density which is desired in both the non-expanded and expanded states. Once a particular geometry is decided upon, such shape may be engraved into the mandrel by techniques which are guided by the designing computer. Once formed in the mandrel, the reverse image of the desired stent may be filled with the stent-forming material to yield stents of specific size and shape such as that shown by way of illustrative examples in FIGS. 8 and 9.

As previously mentioned, the present invention allows for total design freedom of the micro-sized stents and endoprostheses. Optimization can be performed by computer modeling and reduced to practice using computer operated machinery. Various materials can be combined in sandwich layers or composites. For example, the mandrel can be formed of an inner core of a sufficiently solid and dense polymer, such as polyurethane, polyesters, or other similar materials and then covered with a metal surface which meets the aforementioned characteristics for engraving and dissolving. Alternatively, if the mandrel meets the requirements of the present invention, it may be entirely made of a polymer sufficiently made to be conductive.

Stents can be made in various diameter sizes and wall thicknesses. For example, in the 8–12 mm diameter range, wall thicknesses can be in the range of about 0.005 inches. Wall thickness sometimes referred to as strut thickness, of the stent will of course be determined by the type of material, geometric shape and configuration of the open-celled or wire formed structure. In vascular applications, wall or strut thicknesses can range from about 0.0025 inches (0.0635 mm) to about 0.07 inches (0.10 mm). Vascular stent sizes may vary from 3 mm to about 12 mm in diameter.

Various changes to the foregoing described and shown structures would now be evident to those skilled in the art. Accordingly, the particularly disclosed scope of the invention is set forth in the following claims.

What is claimed:

1. A method of forming an elongate expandable intraluminal prosthesis comprising the steps of:

providing a dissolvable elongate mandrel having a metallic electro-deposition accommodating exterior surface portion;

engraving a precise open-celled pattern of voids in said surface portion of said mandrel to define a reverse image of said expandable prosthesis;

electrochemically depositing a prosthesis-forming metallic medium into said engraved open-celled voids of said dissolvable mandrel; and dissolving said mandrel to leave remaining said expandable prosthesis formed by said prosthesis-forming medium.

2. A method of claim 1 wherein said electrochemically depositing step includes:

electrochemically pulse plating said voids with said prosthesis-forming material.

3. A method of claim 1 wherein said electrochemically depositing step further includes depositing said prosthesis-forming medium over said surface portion of said mandrel as well as into said voids.

4. A method of claim 3 wherein said method further includes:

removing said prosthesis-forming material from said surface portion of said mandrel with said prosthesis-forming material remaining in said voids.

5. A method of claim 4 wherein said removing step includes:

machining said surface portion of said mandrel to remove said prosthesis-forming material therefrom.

* * * * *